US011661929B1

(12) United States Patent
Campbell et al.

(10) Patent No.: US 11,661,929 B1
(45) Date of Patent: May 30, 2023

(54) SUCTION VALVE APPARATUS AND METHOD OF USING SAME

(71) Applicants: John H. Campbell, Lafayette, LA (US); Angela Guidry Sobiesk, Lafayette, LA (US)

(72) Inventors: John H. Campbell, Lafayette, LA (US); Angela Guidry Sobiesk, Lafayette, LA (US)

( * ) Notice: Subject to any disclaimer, the term of this patent is extended or adjusted under 35 U.S.C. 154(b) by 222 days.

(21) Appl. No.: 16/937,840

(22) Filed: Jul. 24, 2020

Related U.S. Application Data

(60) Provisional application No. 62/878,119, filed on Jul. 24, 2019.

(51) Int. Cl.
| | |
|---|---|
| *F04B 1/0456* | (2020.01) |
| *F04B 53/10* | (2006.01) |
| *A61M 1/00* | (2006.01) |

(52) U.S. Cl.
CPC ............ *F04B 1/0456* (2013.01); *A61M 1/741* (2021.05); *F04B 53/1002* (2013.01); *F04B 53/1075* (2013.01)

(58) Field of Classification Search
CPC ............ A61M 1/362265; A61M 1/743; A61M 1/782; A61M 5/00; A61M 5/16881; A61M 2005/3128; A61M 2005/5053; A61M 16/20; A61M 25/0075; A61M 25/10185; F16K 25/00; F16K 41/026; F16K 5/06; F16K 5/0642; F16K 5/0631; F16K 5/0647; F24F 11/84
See application file for complete search history.

(56) References Cited

U.S. PATENT DOCUMENTS

| | | | | |
|---|---|---|---|---|
| 133,215 | A * | 11/1872 | Endicott | F16K 31/52408 251/315.08 |
| 849,121 | A * | 4/1907 | Ge Frorer | F16K 5/0647 251/288 |
| 5,256,160 | A * | 10/1993 | Clement | B01J 37/10 604/319 |
| 5,882,194 | A * | 3/1999 | Davis | A61C 1/088 433/91 |
| 6,203,321 | B1 * | 3/2001 | Helmer | A61C 17/125 433/95 |
| 2007/0215828 | A1 * | 9/2007 | Cellemme, Jr. | F16K 5/0642 251/148 |
| 2010/0082016 | A1 * | 4/2010 | Graham | F16K 5/0647 604/537 |

(Continued)

*Primary Examiner* — Adam Marcetich
(74) *Attorney, Agent, or Firm* — Ted M. Anthony; Sarah B. Dupont

(57) ABSTRACT

The present invention pertains to a suction valve apparatus for use in being directly connected to a surgical suction tubing and a surgical suction tip, and thus, allowing a user to stop, or shut off, a flow of suction with the use of a single hand. The present invention pertains to a thumb-activated shut-off valve apparatus for use in easily and efficiently stopping and starting a flow of suction during surgical operations. The suction valve apparatus of the present invention generally comprises a ball valve member, an O-ring, a housing member, and a handle switch member, wherein said ball valve member, said housing member, said O-ring, and said handle switch member cooperate to be able to stop or start a flow of suction from a surgical suction tube and a surgical suction tip.

10 Claims, 11 Drawing Sheets

(56) References Cited

U.S. PATENT DOCUMENTS

| | | | | |
|---|---|---|---|---|
| 2010/0207046 A1* | 8/2010 | Wenchell | ............ | B67D 7/0294 |
| | | | | 251/315.1 |
| 2012/0003603 A1* | 1/2012 | Hirsch | ................ | A61C 17/022 |
| | | | | 433/32 |
| 2012/0259300 A1* | 10/2012 | Bjerregaard | .......... | F16K 5/0407 |
| | | | | 604/327 |
| 2016/0287770 A1* | 10/2016 | Weigand | ............... | A61M 39/00 |

\* cited by examiner

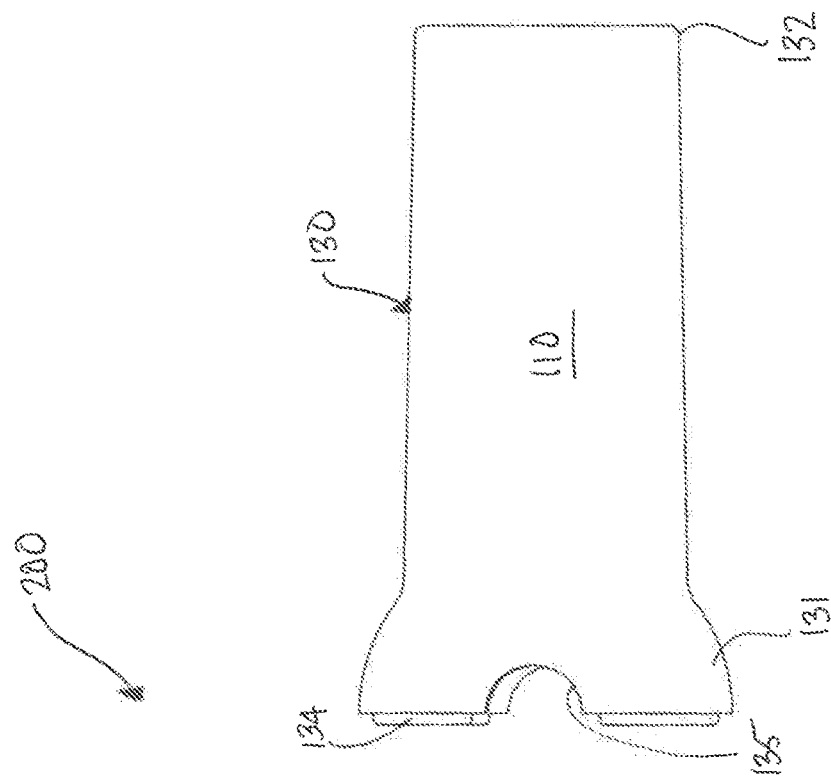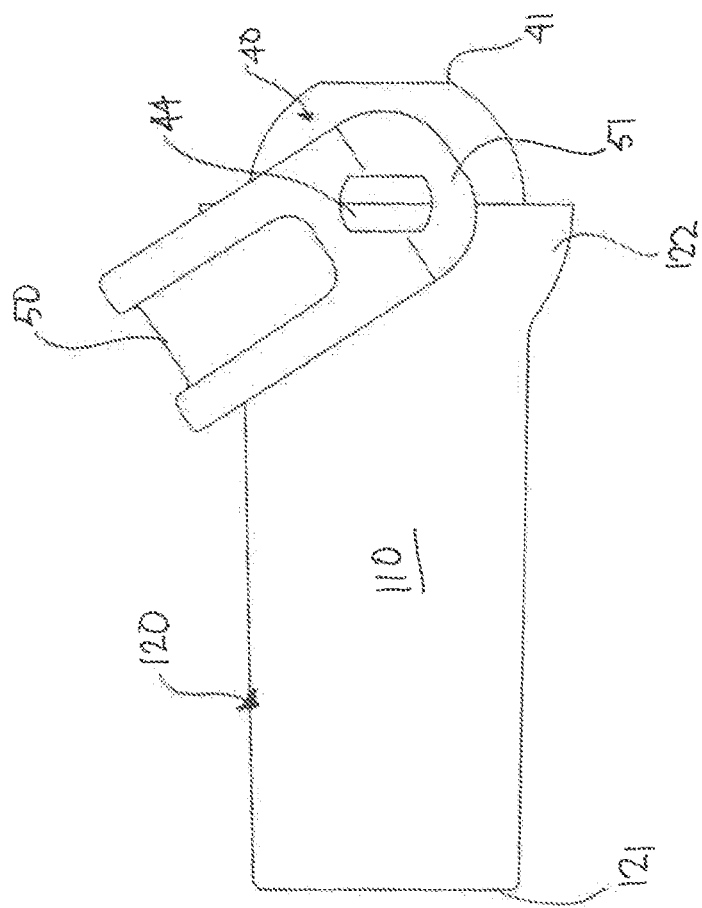
Fig. 10

SUCTION VALVE APPARATUS AND METHOD OF USING SAME

BACKGROUND OF THE INVENTION

Field of the Invention

The present invention pertains to a device for use in stopping and starting a flow of suction, such as, for example, a flow of suction during a variety of different surgical cases and settings. More particularly, the present invention pertains to a thumb-activated shut-off valve apparatus for use in easily and efficiently stopping and starting a flow of suction during surgical operations.

Brief Description of the Prior Art

In medicine, different types of devices are sometimes used in order to create suction. In surgery, suction can be used to remove blood, or other fluids, from a particular area that is being operated on, and thus, allows surgeons to be able to view and work on that particular area. A suction tip is a device that is typically placed within a surgical patient in order to remove said fluids directly.

Suction devices can typically be mechanical hand pumps, or other battery or electrically operated mechanisms. In many hospitals and other health facilities, suction is typically provided by suction regulators that are generally connected to a central medical vacuum supply by way of a pipeline, or tubing, system. Generally, said surgical suction tip is connected to said tubing, which is then attached to a suction device, thereby cooperating together in order to provide suction.

During surgical cases, the noise and humming of a surgical suction can be extremely distracting to surgeons, nurses, and other additional personnel present within an operating room. Typically, most surgeons or surgical nurses will clamp a suction tube with a hemostat, a clamp, or any other similar surgical instrument, in order to eliminate any distracting or annoying sound from said suction, particularly, during a stressful or technical case. However, clamping the suction tubing with a surgical instrument generally requires the use of two hands and requires extra time in order to locate the clamp and then unclamp the suction tubing.

SUMMARY OF THE INVENTION

The present invention comprises a suction valve apparatus for use in being directly connected between a surgical suction tip and a surgical suction tubing, and thus, allowing a user to stop, or shut off, a flow of suction with the use of a single hand. Said suction valve apparatus of the present invention generally comprises a ball valve member, a housing member, an O-ring member, a handle switch member, and a connector member. Said housing member comprises a first end, a second end, and a cavity wherein said ball valve is received and positioned within said housing member. By way of illustration, but not limitation, both said first end and said second end attachably connect to a surgical suction hose and tip, thereby being able to retrofit onto said suction hose, and thus, interrupt any air flow within said suction hose by way of being placed between said suction hose, or tube, and said suction tip. However, it is to be observed that said suction valve apparatus can also be manufactured directly into a surgical suction hose line.

Said ball valve member comprises a substantially ball-like configuration, wherein said ball is received within said cavity of said housing member. Said ball valve further comprises a plurality—typically two (2)—holes on opposing sides of said ball, wherein said holes allow air flow to move through said ball, and ultimately, said suction valve apparatus, when said suction valve apparatus is in an "on" position. Additionally, when said suction valve apparatus is in an "off" position, said holes are moved to a position wherein said holes are covered by an interior surface of said cavity, thereby preventing any air flow from moving through said holes, thus, stopping and shutting off air flow, and suction, of said surgical suction hose.

Said handle switch member comprises a handle-like member, wherein said handle is attachably connected to said ball valve within said housing member. Said handle member is able to be moved in a back and forth motion relative to said suction hose, thereby being able to internally move said ball valve into a desired position. As such, when a user wants to shut off air flow to said surgical suction hose, said user would place his or her thumb on said handle switch member and then move said handle switch member in a desired direction with said thumb in order to move said ball valve, and thus, move said holes within said ball valve in order to prevent air flow from moving through said suction valve apparatus of the present invention. Moreover, said user can move said handle switch member in an opposite direction in order to turn on air flow, and thus, restart said air flow within said surgical suction hose by way of said suction valve apparatus of the present invention.

BRIEF DESCRIPTION OF THE DRAWINGS/FIGURES

The foregoing summary, as well as any detailed description of the preferred embodiments, is better understood when read in conjunction with the drawings and figures contained herein. For the purpose of illustrating the invention, the drawings and figures show certain preferred embodiments. It is understood, however, that the invention is not limited to the specific methods and devices disclosed in such drawings or figures.

FIG. 9A depicts a perspective view of an alternate embodiment of a first end of a housing member of a suction valve apparatus of the present invention.

FIG. 9B depicts a perspective view of an alternate embodiment of a second end of a housing member of a suction valve apparatus of the present invention.

FIG. 10 depicts a side view of an alternate embodiment of a suction valve apparatus of the present invention, wherein a housing member is in a disconnected configuration.

DETAILED DESCRIPTION OF A PREFERRED EMBODIMENT

Figure 1:
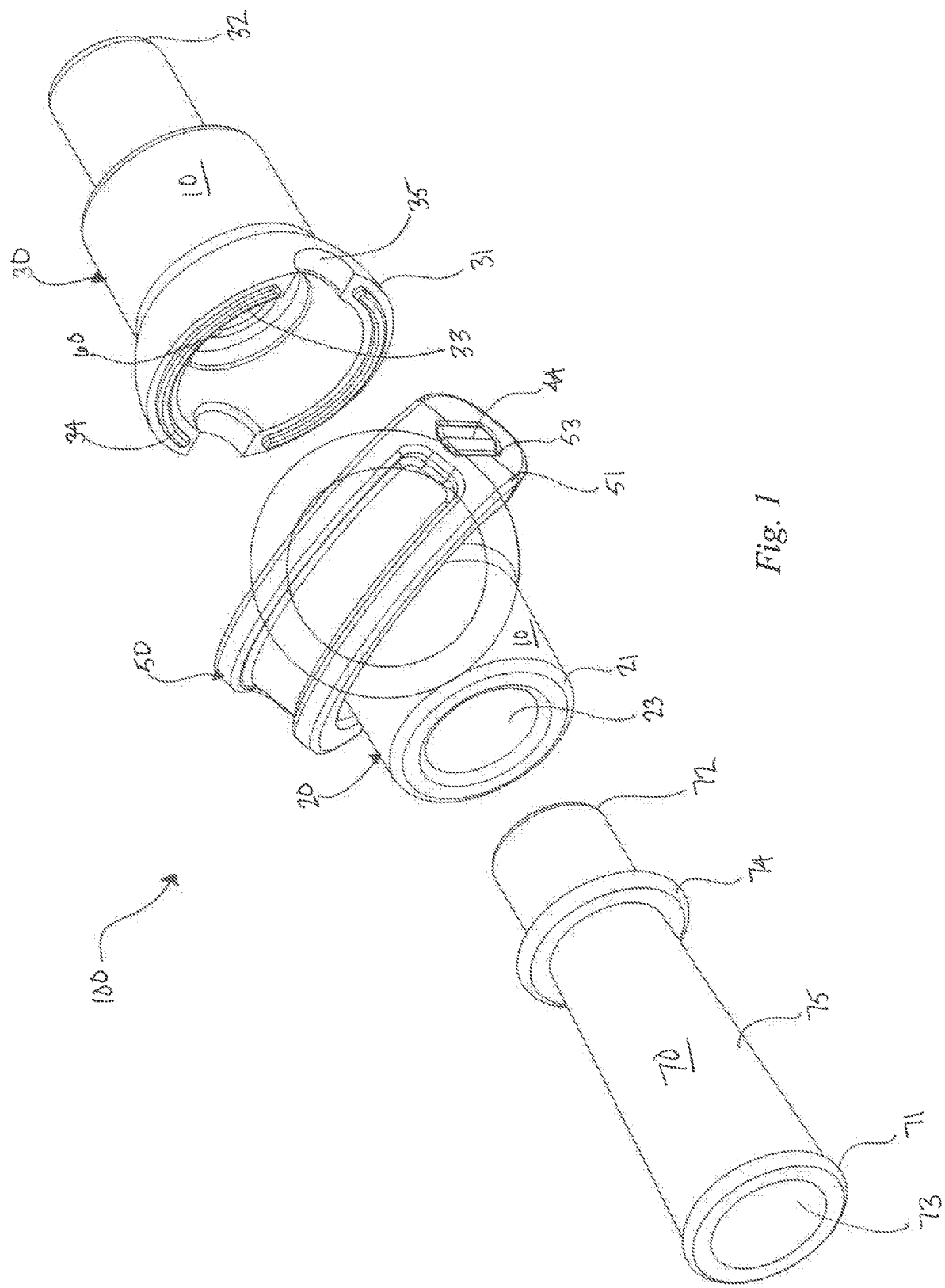
FIG. 1 depicts an exploded perspective view of a preferred embodiment of a suction valve apparatus of the present invention.

Referring to the drawings, the present invention comprises a suction valve apparatus 100 for use in being able to be connected directly to a surgical suction tubing and a suction tip, and thus, allowing a user to stop, or shut off, a flow of suction with the use of a single hand. By way of illustration, but not limitation, said suction valve apparatus 100 of the present invention can be manufactured from a substantially rigid and durable material, such as, for example, a plastic material, or any other similar material exhibiting like characteristics.

In the context of this discussion herein, the distal position is said to be "away from" a surgical patient and the proximal position is said to be "closer to" a surgical patient. Moreover, in the context of this discussion herein, the handle switch member 50 is said to be in an "on" position when said handle switch member 50 is in a proximal position, and said handle switch member 50 is said to be in an "off" position when said handle switch member 50 is in a distal position. However, it is to be observed that the orientation of the suction valve apparatus 100 could be reversed, wherein a handle switch member 50 could be in an "on" position when said handle switch member 50 is in a distal position and could be in an "off" position when said handle switch member 50 is in a proximal position.

In a preferred embodiment, FIG. 1 depicts an exploded perspective view of a preferred embodiment of a suction valve apparatus 100, generally comprising a housing member 10, a ball valve member 40, an O-ring member 60, a handle switch member 50, and a connector member 70, wherein said housing member 10 comprises a female connection end 20 and a male connection end 30, and wherein said female connection end 20 and said male connection end 30 attachably connect to each other.

Said female connection end 20 of said housing member 10 comprises a substantially tubular member having a first end 21, a second end 22, and an internal channel 23. Said first end 21 of said female end 20 of said housing member 10 attachably connects to said connector member 70, wherein said connector member 70 connects to a surgical suction tip in order to allow for continuous fluid flow through said suction tip, said internal channel 23 of said suction valve apparatus 100, and a surgical suction tube. Said second end 22 of said female end 20 of said housing member 10 comprises a notch 24 for use in attachably connecting to said male end 30 of said housing member 10.

Moreover, said second end 22 comprises a substantially cupped reservoir in order to receive and position said ball valve member 40 in conjunction with said male end 30 of said housing member 10. Additionally, second end 22 comprises a plurality—typically two (2)—of grooves 25, wherein an arm member 44 of said ball valve member 40 can be received. Although not depicted in FIG. 1, second end 22 of female connection 20 of housing member 10 further comprises an O-ring 60, wherein said O-ring 60 helps seal ball valve member 40, and thus prevents any fluid leakage.

Said male connection end 30 of said housing member 10 comprises a substantially tubular member having a first end 31, a second end 32, and an internal channel 33. Said second end 32 of said male end 30 of said housing member 10 comprises a substantially smaller outer diameter than said first end 31 of said male end 30, thereby allowing said second end 32 to be received within a surgical suction tube, and thus, attachably connect to said surgical suction tube in order to allow for continuous fluid flow through said suction tube, said internal channel 33 of said suction valve apparatus 100, and said suction tip. Said first end 31 of said male end 30 of said housing member 10 comprises an outwardly extending latch 34 for use in attachably connecting to said female end 20 of said housing member 10.

Moreover, said first end 31 comprises a substantially cupped reservoir for use in receiving and positioning said ball valve member 40 in conjunction with said female end 20 of said housing member 10. Additionally, first end 31 comprises a plurality—typically two (2)—of grooves 35, wherein an arm member 44 of said ball valve member 40 can be received. First end 31 of male connection 30 of housing member 10 further comprises an O-ring 60, wherein said O-ring 60 helps seal ball valve member 40, and thus prevents any fluid leakage.

Said first end 31 of said male connection end 30 and said second end 22 of said female connection end 20 are attachably connected by way of said latch 34 and said notch 24, wherein said female end 20 and said male end 30 cooperate to form a spherical shell 12 comprising an internal cavity 13, or reservoir, wherein said ball valve member 40 is received and positioned.

By way of illustration, but not limitation, it is to be observed that a length of one connection end (either female connection end 20 or male connection end 30) may be relatively shorter than a length of the other connection end. The connection end having a shorter length would be able to receive connector member 70, wherein said connector member 70 could be manufactured from a substantially rubber material, or any other material exhibiting like characteristics. Said connector member 70 can be used in facilitating in the connection between said surgical tip and said suction valve apparatus 100 of the present invention. As such, said connector member 70 provides additional flexibility to said suction valve apparatus 100 by way of being able to accept and receive a variety of different types of surgical suction tips.

Figure 2:
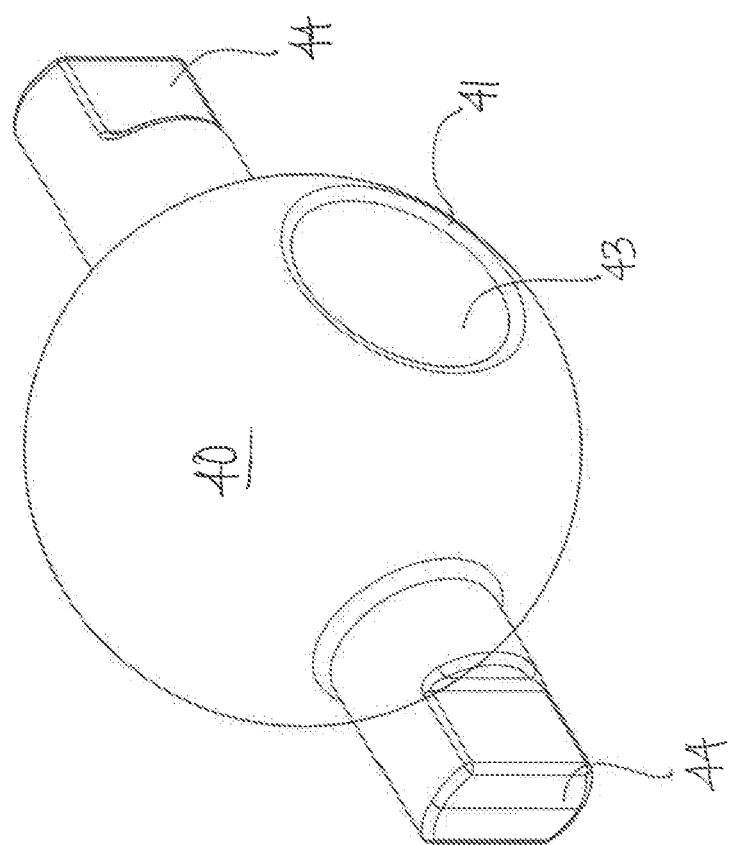
FIG. 2 depicts a perspective view of a preferred embodiment of a ball valve member of a suction valve apparatus of the present invention.

FIG. 2 depicts a perspective view of said ball valve member 40 of said suction valve apparatus of the present invention. Said ball valve apparatus 40 comprises a substantially spherical member having a first void 41 and a second void 42 (although second void 42 is not depicted in FIG. 2, it is to be observed that second void 42 is in a directly opposite position from first void 41). Said first void 41 and said second void 42 are connected by way of an inner cavity 43 that allows for fluid to flow through when said ball valve apparatus 40 is positioned in an "on" orientation. Said ball valve member 40 further comprises a plurality of—typically (2)—arm members 44, wherein said arm members 44 extend in a substantially outward and perpendicular orientation from said ball valve member 40. Said arm members 44 attachably connect to said handle switch member 50, thereby creating a cohesive unit between said ball valve member 40 and said handle switch member 50. Thus, as said handle switch member 50 is moved and operated (as discussed below), said ball valve member 40 is likewise moved and operated into a desired position.

Figure 3:
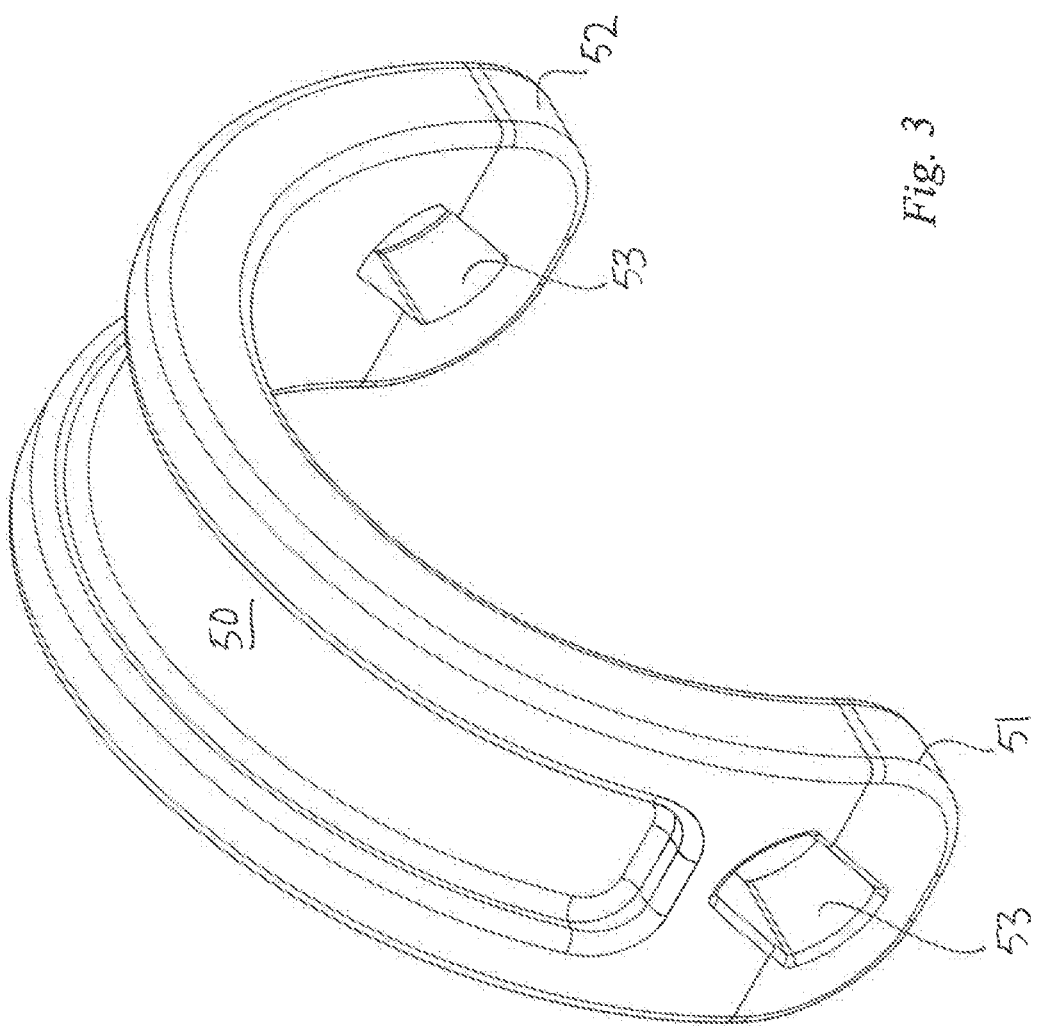
FIG. 3 depicts a perspective view of a preferred embodiment of a handle switch member of a suction valve apparatus of the present invention.

FIG. 3 depicts a perspective view of said handle switch member 50 of the present invention. Said handle switch member 50 comprises a substantially curved shape, having a first end 51 and a second end 52. Said first end 51 and said second end 52 each comprise a void 53, wherein said arm members 44 of said ball valve member 40 are received within said voids 53, thereby attachably connecting said handle switch member 50 to said ball valve member 40. Said handle switch member 50 is used as an operational component of said suction valve apparatus 100, wherein a user is able to flip said handle switch member 50 into either a proximal position or a distal position, relative to said surgical suction tip. As a result, said user is able to either "turn on" or "turn off" the flow of said suction by way of operating and flipping said handle switch member 50 of said surgical valve apparatus 100 of the present invention, which in turn moves and operates said ball valve member 40 in order to either "turn on" or "turn off" the flow of said suction.

Figure 4:
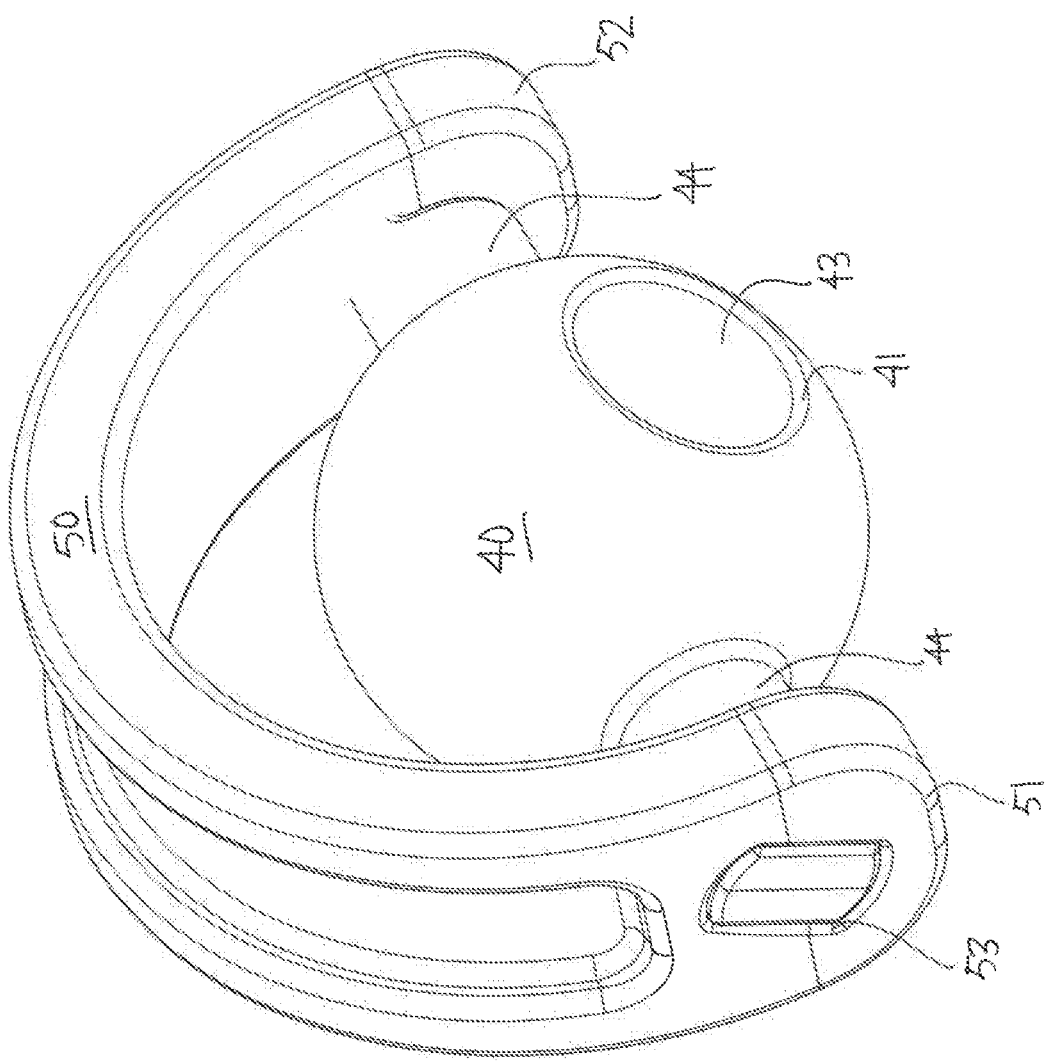
FIG. 4 depicts a perspective view of a preferred embodiment of a ball valve member and a handle switch member of a suction valve apparatus of the present invention, wherein said ball valve member and said handle switch member are in an attachably connected configuration.

FIG. 4 depicts a perspective view of said ball valve member 40 and said handle switch member 50 attachably connected by way of said arm members 44 and said voids 53. Arm members 44 of said ball valve member 40 are received within voids 53 located on both said first end 51 and said second end 52 of said handle switch member 50, thereby creating a cohesive unit that can move simultaneously and in conjunction with each other.

Figure 5:
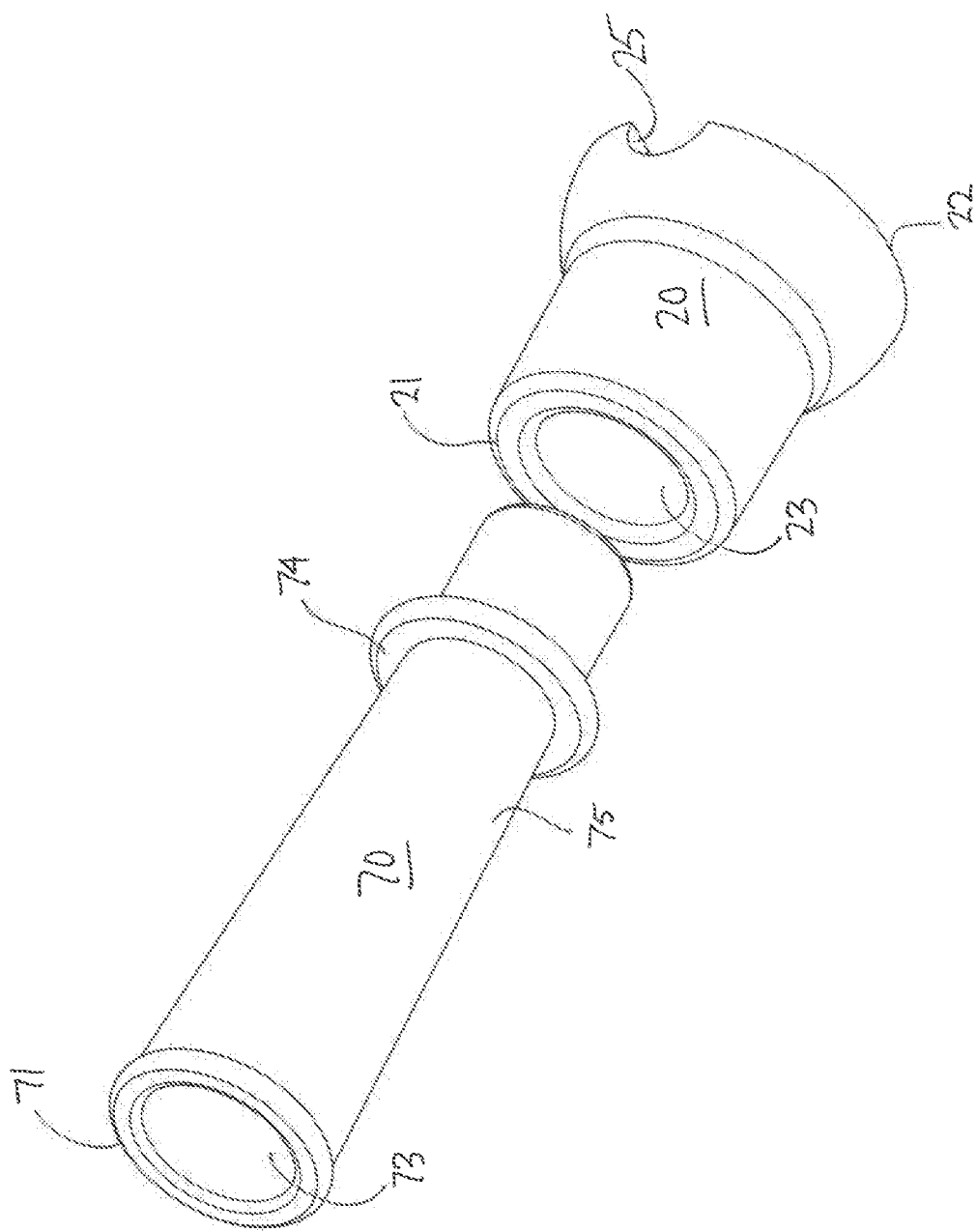
FIG. 5 depicts a perspective view of a preferred embodiment of a connector member of the present invention, wherein said connector member can attachably connect to a housing member of a suction valve apparatus of the present invention.

FIG. 5 depicts a perspective view of said connector member 70 attachably connecting to said female connection end 20 of said housing member 10, wherein said connector member 70 allows for more flexibility in being able to accept and attachably connect to a variety of different types of surgical suction tips. For the purposes of this description herein, connector member 70 attachably connects to female connection end 20; however, it is to be observed that in an alternate embodiment, connector member 70 could also attachably connect to male connection end 30. Connector member 70 comprises a substantially cylindrical tube member, wherein said connector member 70 can be manufactured from a substantially flexible and rubber material, or any other similar material exhibiting like characteristics.

Said connector member 70 comprises a first end 71, a second end 72, and an inner channel 73, wherein said connector member 70 has a substantially tapered configuration. Said first end 71 comprises a relatively larger diameter and attachably connects to said surgical tip, and said second end 72 comprises a relatively smaller diameter and attachably connects to said first end 21 of said female connection end 20. Connector member 70 further comprises an O-ring 74 that adjacently fits around an outer surface 75 of said connector member 70. Said O-ring 74 creates a seal with said first end 21 of said female end 20, thereby preventing any fluid from leaking out of said tubing and said suction valve apparatus 100 of the present invention.

Figure 6:
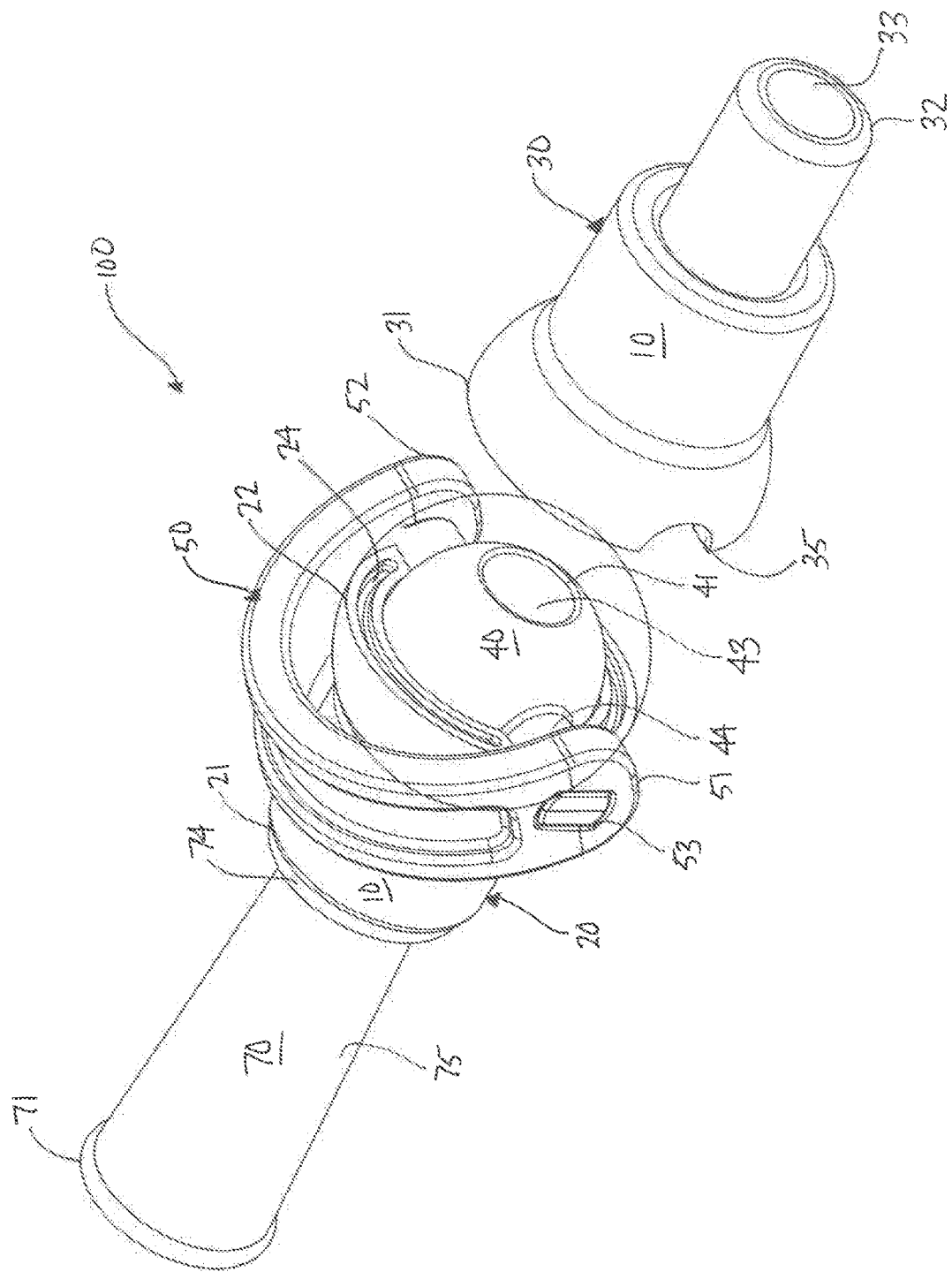
FIG. 6 depicts a perspective view of a preferred embodiment of a suction valve apparatus of the present invention, wherein a housing member is in a disconnected configuration.

FIG. 6 depicts a perspective view of said suction valve apparatus 100, generally comprising said housing member 10, said ball valve member 40, said handle switch member 50, and said connector member 70, wherein said housing member 10 comprises said female connection end 20 and said male connection end 30. Said female connection end 20 comprises said first end 21, said second end 22, and said internal channel 23, wherein said first end 21 is attachably connected to said second end 72 of said connector member 70 and said second end 22 is attachably connected to said male end 30.

Said male connection end 30 comprises said first end 31, said second end 32, and said internal channel 33, wherein said second end 32 is attachably connected to said surgical tubing and said first end 31 is attachably connected to said female end 20. Said female end 20 comprises said notch 24, and said male end 30 comprises said latch 34, wherein said notch 24 and said latch 34 mate together in order to attachably connect said female end 20 to said male end 30. As such, said female end 20 and said male end 30 attachably connect and cooperate to form said spherical shell 12 having an internal cavity 13, wherein said ball valve member 40 is received and positioned within said internal cavity 13.

Additionally, said connector member 70 comprises first end 71, second end 72, and inner channel 73, wherein said connector member 70 has a substantially tapered configuration. Said first end 71 comprises a relatively larger diameter and attachably connects to said surgical tip, and said second end 72 comprises a relatively smaller diameter and attachably connects to said first end 21 of said female connection end 20. Connector member 70 further comprises O-ring 74 that adjacently fits around outer surface 75 of said connector member 70. Said O-ring 74 creates a seal with said first end 21 of said female end 20, thereby preventing any fluid from leaking out of said tubing and said suction valve apparatus 100 of the present invention.

Said ball valve member 40 comprises a substantially spherical shape, having a plurality of arms 44 extending in a perpendicular direction from an outer surface 45 of said ball valve member 40. Said arm members 44 are received and positioned within said grooves 25 of said female end 20 and said grooves 35 of said male end 30 of said housing member 10. Additionally, said arm members 44 attachably connect to said handle switch member 50 by way of said voids 53 of said handle switch member 50. Said handle switch member 50 cooperates with and thus creates a cohesive unit with said ball valve member 40, and thus, when a user moves said handle switch member 50, said ball valve member 40 is also moved respectively.

Said ball valve member 40 further comprises a plurality of bores 41, 42, wherein said bores 41, 42 are positioned on an axis opposite from each other, but are connected by way of an internal channel 43. When said handle switch member 50 is positioned in a proximal orientation relative to said surgical suction tip and surgical patient, said bores 41, 42, and thus, said internal channel 43 of said ball valve member 40 are axially aligned with said internal channel 23 of said female end 20 and said internal channel 33 of said male end 30 of said housing member 10. Thus, said internal channels 23, 33 of said housing member 10 and said internal channel 43 of said ball valve member 40 allow for the flow of fluid to continue through said ball valve member 40 when said handle switch member 50 is positioned in a proximal orientation relative to said surgical suction tip, or in an "on" configuration, and thus, surgical suction is allowed to continue and flow.

When said handle switch member 50 is flipped, or moved, into a distal position relative to said surgical suction tip and said surgical patient, said handle switch member 50, and thus, said ball valve member 40, are moved into an "off" configuration. As such, said ball valve member 40 rotates, thereby moving said bores 41, 42 and said internal channel 43 of said ball valve member 40 into an orientation that does not axially align with said internal channels 23, 33 of said housing member 10. As such, O-ring members 60 create a seal with an outer surface of said ball valve member 40, and thus fluid flow from surgical suction is unable to continue to move through said ball valve apparatus 40 of said surgical valve apparatus 100, thereby, stopping said surgical suction.

Figure 7:
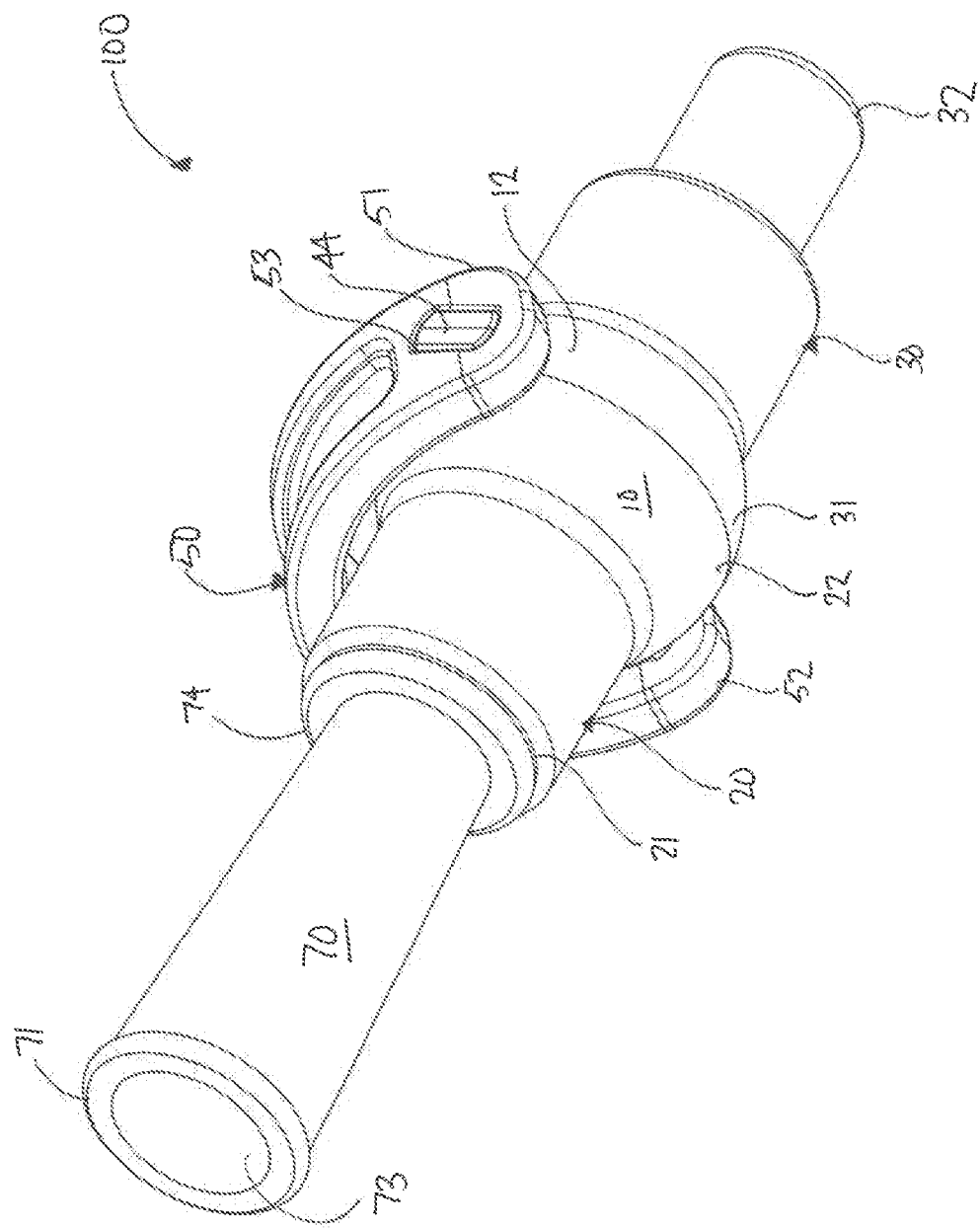
FIG. 7 depicts a perspective view of a preferred embodiment of a suction valve apparatus of the present invention.

FIG. 7 depicts a perspective view of said suction valve apparatus 100 of the present invention, generally comprising said housing member 10, said ball valve member 40, said handle switch member 50, and said connector member 70, wherein said housing member 10 is in a connected configuration. When in operation, a user will attachably connect said suction valve apparatus 100 to a surgical suction tubing and a surgical suction tip. Said surgical tip will be connected to said first end 71 of said connector member 70, and said surgical tubing will be connected to said second end 32 of said male connection 30 of said housing member 10. (It is also to be noted that said suction valve apparatus 100 may also be manufactured directly onto a surgical suction tubing).

During a surgical operation, when the flow of suction is needed, a user (typically a nurse, a surgical assistant, or a physician's assistant) will maintain said handle switch member 50 in a proximal position relative to said surgical suction and said surgical patient. The proximal position of said handle switch member 50 allows said bores 41, 42 and said internal channel 43 of said ball valve member 40 to remain in an axially aligned positioned with said internal channels 23, 33 of said housing member 10, and thus, said surgical suction tip and said suction tubing. As a result, any flow of suction and fluid will continue through said suction valve apparatus 100, while said handle switch member 50 is positioned in an "on" configuration.

When the flow of suction is to be stopped, said user will move said handle switch member 50 into a distal position relative to said surgical suction and said surgical patient. The distal position of said handle switch member 50 allows said ball valve member 40 to rotate, and thus, said bores 41, 42 and said internal channel 43 of said ball valve member 40 to be moved into a position away from said internal channels 23, 33 of said housing member 10 and said surgical suction tubing. As a result, said bores 41, 42 and internal channel 43 of said ball valve apparatus 40 will be blocked by an internal surface 14 of said cavity 13 of said housing member 10, and O-ring members 60 will seal against an outer surface of ball valve member 40, thereby stopping any flow of suction and thus any fluid from said surgical tip and said surgical suction tubing, while said handle switch member 50 is positioned in an "off" configuration.

Figure 8:
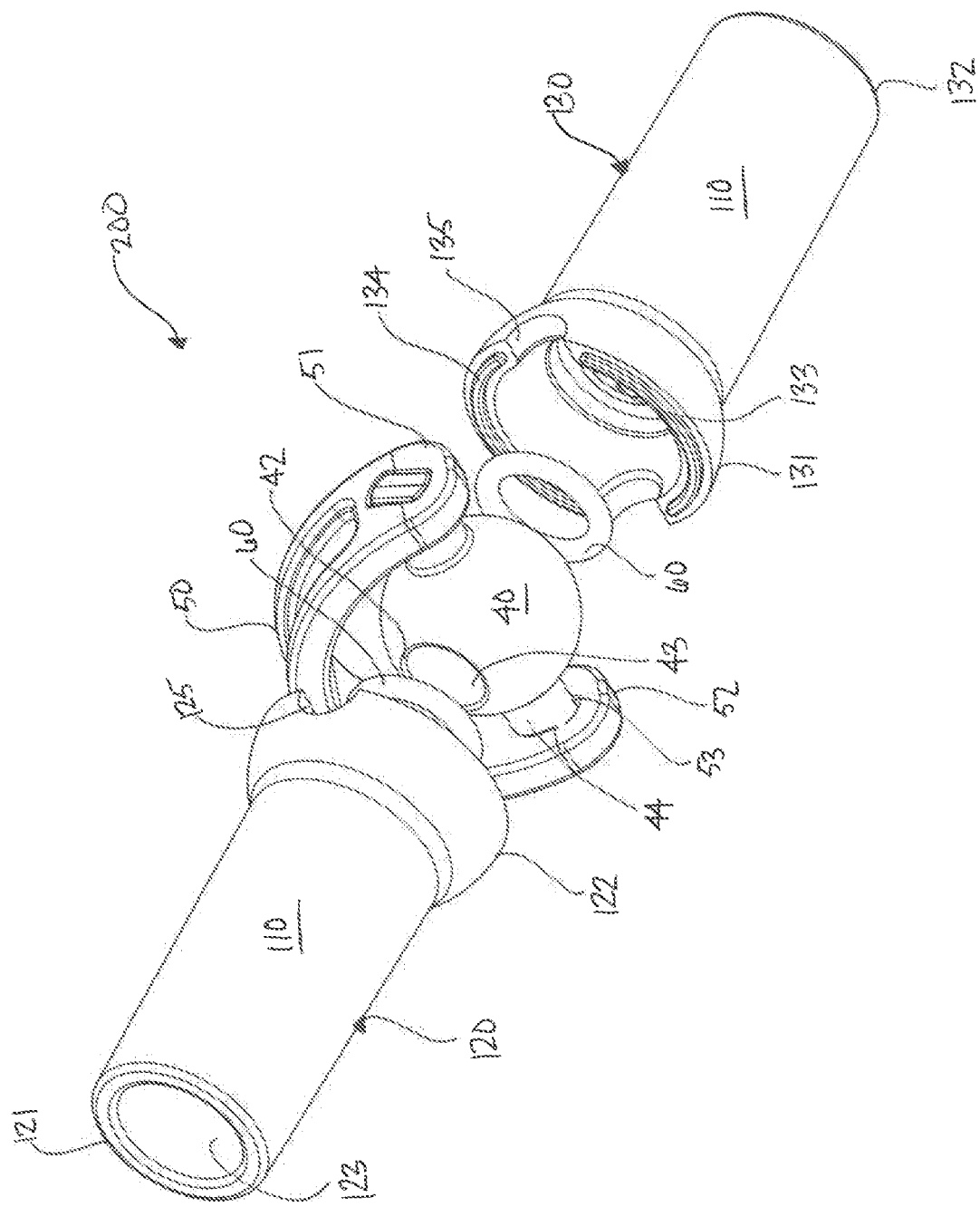
FIG. 8 depicts a perspective view of an alternate embodiment of a suction valve apparatus of the present invention, wherein a housing member is in a disconnected configuration.

In an alternate embodiment, FIG. 8 depicts a perspective view of a suction valve apparatus 200, generally comprising a housing member 110, a ball valve member 40, an O-ring member 60, and a handle switch member 50, wherein said housing member 110 is in a disconnected configuration.

Figure 9:
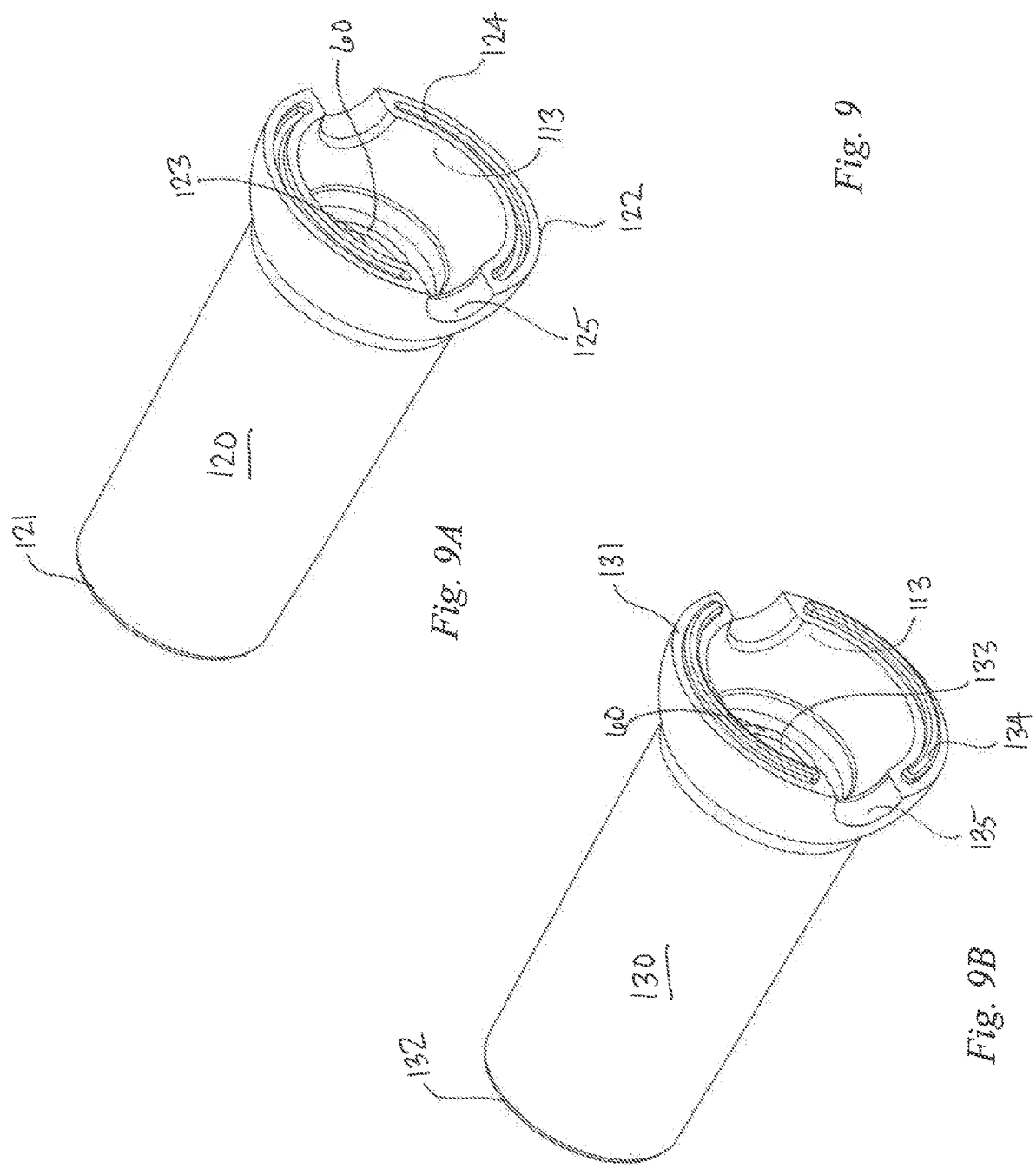
FIG. 9 depicts various views of an alternate embodiment of a housing member of a suction valve apparatus of the present invention.

FIG. 9 depicts various views of an alternate embodiment of said housing member 110 of said suction valve apparatus 200 of the present invention, wherein said housing member 110 comprises a female connection end 120 and a male connection end 130, and wherein said female connection end 120 and said male connection end 130 attachably connect to each other. FIG. 9A depicts a perspective view of an alternate embodiment of said female connection end 120 of said housing member 110 of said suction valve apparatus 200, and FIG. 9B depicts a perspective view of an alternate embodiment said male connection end 130 of said housing member 110 of said suction valve apparatus 200.

Referring to FIG. 9A, said female connection end 120 of said housing member 110 comprises a substantially tubular member having a first end 121, a second end 122, and an internal channel 123. Said first end 121 of said female end 120 of said housing member 110 attachably connects to a surgical suction tip in order to allow for continuous fluid flow through said suction tip and said internal channel 123 of said suction valve apparatus 200. Said second end 122 of said female end 120 of said housing member 110 comprises a notch 124 for use in attachably connecting to said male end 130 of said housing member 110.

Moreover, said second end 122 comprises a substantially cupped reservoir in order to receive and position said ball valve member 40 in conjunction with said male end 30 of said housing member 110. Additionally, second end 122 comprises a plurality—typically two (2)—of grooves 125, wherein an arm member 44 of said ball valve member 40 can be received. Second end 122 of female connection 120 of housing member 110 further comprises an O-ring 60, wherein said O-ring 60 helps seal ball valve member 40, and thus prevents any fluid leakage.

Referring to FIG. 9B, said male connection end 130 of said housing member 110 comprises a substantially tubular member having a first end 131, a second end 132, and an internal channel 133. Said second end 132 of said male end 130 of said housing member 110 attachably connects to a surgical suction tube in order to allow for continuous fluid flow through said suction tube and said internal channel 133 of said suction valve apparatus 200. Said first end 131 of said male end 130 of said housing member 110 comprises an outwardly extending latch 134 for use in attachably connecting to said female end 120 of said housing member 110.

Moreover, said first end 131 comprises a substantially cupped reservoir for use in receiving and positioning said ball valve member 40 in conjunction with said female end 120 of said housing member 110. Additionally, first end 131 comprises a plurality—typically two (2)—of grooves 135, wherein an arm member 44 of said ball valve member 40 can be received. First end 131 of male connection 130 of housing member 110 further comprises an O-ring 60, wherein said O-ring 60 helps seal ball valve member 40, and thus prevents any fluid leakage.

Said first end 131 of said male connection end 130 and said second end 122 of said female connection end 120 are attachably connected by way of said latch 134 and said notch 124, wherein said female end 120 and said male end 130 cooperate to form a spherical shell 112 comprising an internal cavity 113, or reservoir, wherein said ball valve member 40 is received and positioned.

In an alternate embodiment, FIG. 10 depicts a side view of said suction valve apparatus 200 of the present invention, comprising a housing member 110, a ball valve member 40, and a handle switch member 50. Referring to FIG. 10, and also referring back to FIG. 8, said housing member 110 comprises said female connection end 120 and said male connection end 130. Said female connection end 120 comprises said first end 121, said second end 122, and said internal channel 123, wherein said first end 121 is attachably connected to said surgical suction tip and said second end 122 is attachably connected to said male end 130. Said male connection end 130 comprises said first end 131, said second end 132, and said internal channel 133, wherein said second end 132 is attachably connected to said surgical tubing and said first end 131 is attachably connected to said female end 120. Said female end 120 comprises said notch 124, and said male end 130 comprises said latch 134, wherein said notch 124 and said latch 134 mate together in order to attachably connect said female end 120 to said male end 130. As such, said female end 120 and said male end 130 attachably connect and cooperate to form said spherical shell 112 having an internal cavity 113, wherein said ball valve member 40 is received and positioned within said internal cavity 113.

Said ball valve member 40 comprises a substantially spherical shape, having a plurality of arms 44 extending in a perpendicular direction from an outer surface 45 of said ball valve member 40. Said arm members 44 are received and positioned within said grooves 125 of said female end 120 and said grooves 135 of said male end 130 of said housing member 110. Additionally, said arm members 44 attachably connect to said handle switch member 50 by way of said voids 53 of said handle switch member 50. Said handle switch member 50 cooperates with and thus creates a cohesive unit with said ball valve member 40, and thus, when a user moves said handle switch member 50, said ball valve member 40 is also moved respectively.

Figure 11:
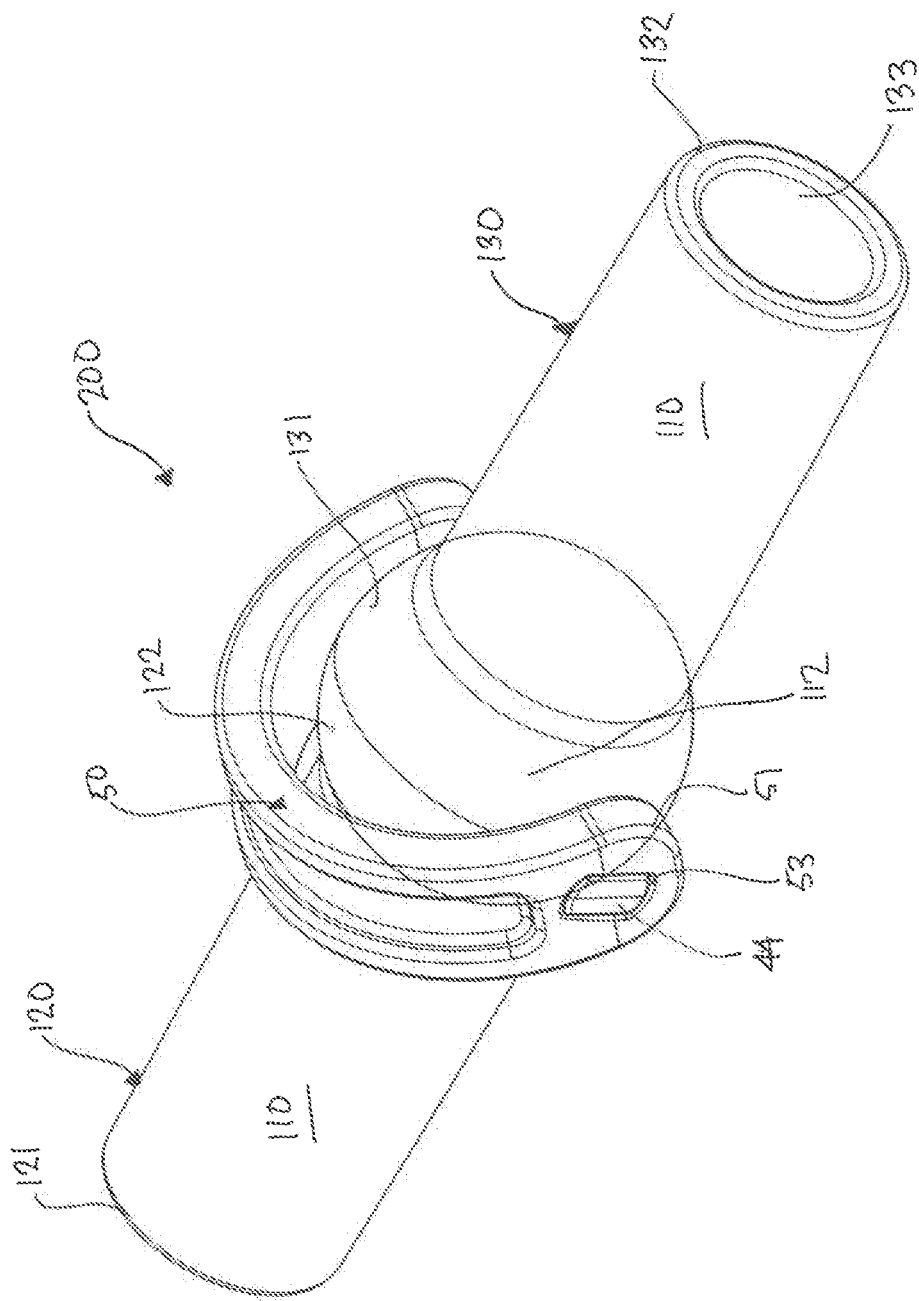
FIG. 11 depicts a perspective view of an alternate embodiment of a suction valve apparatus of the present invention.

FIG. 11 depicts a perspective view of said suction valve apparatus 200 of the present invention, generally comprising said housing member 110, said ball valve member 40, and said handle switch member 50, wherein said housing member 110 is in a connected configuration. When in operation, a user will attachably connect said suction valve apparatus 200 to a surgical suction tubing and a surgical suction tip. Said surgical suction tip will be connected to said first end 121 of said female connection 120 of said housing member 110, and said surgical suction tubing will be connected to said second end 132 of said male connection 130 of said housing member 110. (It is also to be noted that said suction valve apparatus 100 may also be manufactured directly onto a surgical suction tubing).

The above-described invention has a number of particular features that should preferably be employed in combination, although each is useful separately without departure from the scope of the invention. While the preferred embodiment of the present invention is shown and described herein, it will be understood that the invention may be embodied otherwise than herein specifically illustrated or described, and that certain changes in form and arrangement of parts and the specific manner of practicing the invention may be made within the underlying idea or principles of the invention.

What is claimed:

1. A suction valve apparatus for use in starting and stopping a flow of suction, comprising:
   a. a housing member comprising:
      i. a female connection end having a first end, a second end, an internal channel, and a semi-spherical cavity;
      ii. a male connection end having a first end, a second end, an internal channel, and a semi-spherical cavity, wherein said first end of said male connection end is attachably connected to said second end of said female connection end, thereby forming a fully spherical cavity, and said second end of said male connection end is attachably connected to a surgical suction tube;
   b. a ball valve member, wherein said ball valve member comprises an internal channel and a plurality of arm members, wherein said ball valve member is received within said spherical cavity of said female connection end and said male connection end of said housing member;
   c. a handle member comprising a first end and a second end, wherein said first end and said second end each comprise a bore, wherein said arm members of said ball valve member are received within said bores of said handle member;
   d. a plurality of O-rings, wherein a first O-ring is received within said second end of said female connection end, and a second O-ring is received within said first end of said male connection end; and,
   e. a connector member, wherein said connector member comprises a cylindrical tube having a first end, a second end, an internal channel, and an exterior O-ring, wherein said second end of said connector member attachably connects to a first end of said female connection end and said first end of said connector member attachably connects to a surgical suction tip.

2. The apparatus of claim 1, wherein said second end of said female connection end comprises a notch, and said first end of said male connection end comprises a latch, wherein said notch and said latch mate together as an attachment means.

3. The apparatus of claim 2, wherein said handle member and said ball valve member cooperate to form a cohesive unit, wherein said ball valve member rotates between positions within said housing member when said handle member is moved from a proximal position to a distal position, or vice versa.

4. The apparatus of claim 3, wherein said internal channel of said connector member, said internal channel of said female connection end, said internal channel of said ball valve member, and said internal channel of said male connection end are axially aligned when said handle member is positioned in an "on" configuration in order to allow fluid to flow freely through said suction valve apparatus.

5. The apparatus of claim 3, wherein said internal channel of said ball valve member is not axially aligned with said internal channel of said connector member, said internal channel of said female connection end, and said internal channel of said male connection end when said handle member is positioned in an "off" configuration in order to stop fluid from flowing freely through said suction valve apparatus.

6. A method of starting and stopping a flow of suction during a surgical operation, comprising:
   a. attachably connecting a surgical valve apparatus to a surgical suction tip and a surgical suction tube, wherein said surgical valve apparatus comprises:
      i. a housing member comprising:
         aa. a female connection end having a first end, a second end, an internal channel, and a semi-spherical cavity;
         bb. a male connection end having a first end, a second end, an internal channel, and a semi-spherical cavity, wherein said first end of said male connection end is attachably connected to said second end of said female connection end, thereby forming a fully spherical cavity, and said second end of said male connection end is attachably connected to a surgical suction tube;
      ii. a ball valve member, wherein said ball valve member comprises an internal channel and a plurality of arm members, wherein said ball valve member is received within said spherical cavity of said female connection end and said male connection end of said housing member;
      iii. a handle member comprising a first end and a second end, wherein said first end and said second end each comprise a bore, wherein said arm members of said ball valve member are received within said bores of said handle member;
iv. a plurality of O-rings, wherein a first O-ring is received within said second end of said female connection end, and a second O-ring is received within said first end of said male connection end; and,
v. a connector member, wherein said connector member comprises a cylindrical tube having a first end, a second end, an internal channel, and an exterior O-ring, wherein said second end of said connector member attachably connects to a first end of said female connection end and said first end of said connector member attachably connects to a surgical suction tip;
b. turning on a flow of suction;
c. maintaining said suction valve apparatus in an "on" configuration, wherein said internal channel of said ball valve member is axially aligned with said internal channel of said female connection end and said internal channel of said male connection end; and,
d. flipping said handle switch member to an opposite position, thereby turning said suction valve apparatus into an "off" configuration, wherein said internal channel of said ball valve member moves away from said internal channel of said female connection end and said internal channel of said male connection end.

7. The method of claim 6, wherein said second end of said female connection end comprises a notch, and said first end of said male connection end comprises a latch, wherein said notch and said latch mate together as an attachment means.

8. The method of claim 7, wherein said handle member and said ball valve member cooperate to form a cohesive unit, a ball valve member, wherein said ball valve member comprises an internal channel and a plurality of arm members when said handle member is moved from a proximal position to a distal position, or vice versa.

9. The method of claim 8, wherein said internal channel of said connector member, said internal channel of said female connection end, said internal channel of said ball valve member, and said internal channel of said male connection end are axially aligned when said handle member is positioned in an "on" configuration in order to allow fluid to flow freely through said suction valve apparatus.

10. The method of claim 8, wherein said internal channel of said ball valve member is not axially aligned with said internal channel of said connector member, said internal channel of said female connection end, and said internal channel of said male connection end when said handle member is positioned in an "off" configuration in order to stop fluid from flowing freely through said suction valve apparatus.

* * * * *